United States Patent [19]
Ouchi

[11] Patent Number: 6,113,586
[45] Date of Patent: Sep. 5, 2000

[54] JOINT MECHANISM FOR ENDOSCOPIC TREATMENT INSTRUMENT, AND ENDOSCOPIC TREATMENT SYSTEM USING THAT MECHANISM

[75] Inventor: Teruo Ouchi, Saitama, Japan

[73] Assignee: Asahi Kogaku Kabushiki Kaisha, Tokyo, Japan

[21] Appl. No.: 09/229,679

[22] Filed: Jan. 13, 1999

[30] Foreign Application Priority Data

Jan. 16, 1998 [JP] Japan .................................. 10-006223
Aug. 28, 1998 [JP] Japan .................................. 10-242630

[51] Int. Cl.[7] .............................. A61B 17/00; F16B 2/02; F16B 1/00
[52] U.S. Cl. .............................. 606/1; 403/350; 403/351; 606/49
[58] Field of Search .............................. 606/49, 205, 174, 606/1; 403/350, 351, 372

[56] References Cited

U.S. PATENT DOCUMENTS

| | | | |
|---|---|---|---|
| 4,289,131 | 9/1981 | Mueller | 128/303 |
| 5,152,779 | 10/1992 | Sanagi . | |
| 5,254,117 | 10/1993 | Rigby et al. | 606/46 |
| 5,407,293 | 4/1995 | Crainich | 403/322 |
| 5,931,598 | 8/1999 | Wang | 403/351 |
| 6,045,564 | 4/2000 | Walen | 606/167 |

FOREIGN PATENT DOCUMENTS 5878655 5/1983 Japan .
6031684 9/1985 Japan .

*Primary Examiner*—Linda C. M. Dvorak
*Assistant Examiner*—Jocelyn Debra Ram
*Attorney, Agent, or Firm*—Greenblum & Bernstein, P.L.C.

[57] ABSTRACT

A joint mechanism for connection between a sheath and a manipulating section of an endoscopic treatment instrument is provided. A joint includes a leading end portion connected to said sheath, and an expanded base end portion having a first cross sectional shape. A receptacle ring is mounted on an leading end portion of said manipulating section and rotatable within a predetermined angular range relative to said leading end portion of said manipulating section. The receptacle ring is formed with an insertion hole having such a second cross section as to permit said expanded base end portion to be passed therethrough. A fitting hole is formed in said leading end portion of said manipulating section so as to non-rotatably receiving said expanded base end portion that has been passed through the insertion hole. By rotating said receptacle ring in a state that said expanded base end portion has been passed through said insertion hole and fitted in said fitting hole, said insertion hole is oriented to inhibit passage of said expanded base end portion therethrough, thereby non-removably connect said joint to said leading end portion of said manipulating section.

22 Claims, 17 Drawing Sheets

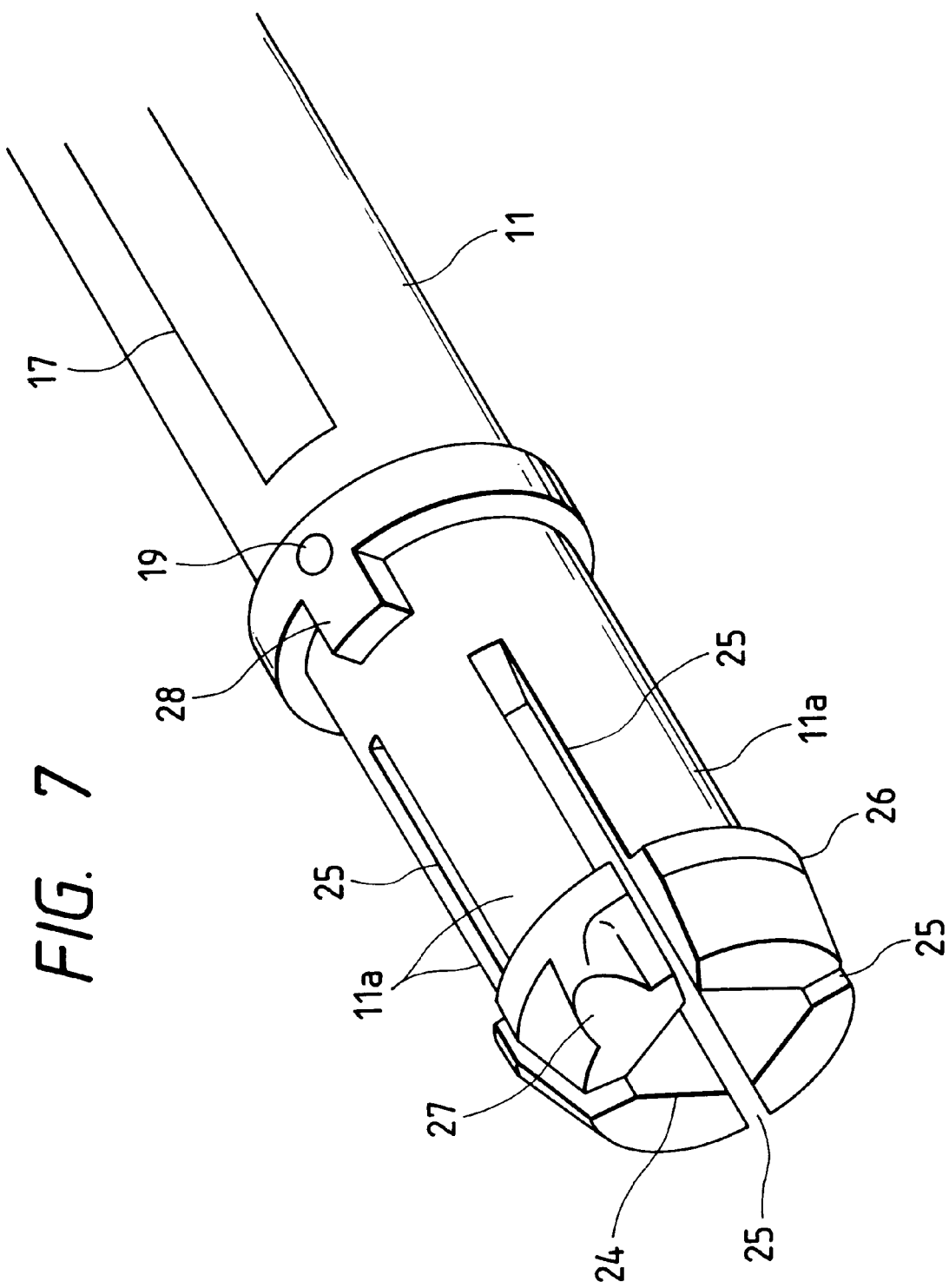

HF MANIPULATOR

HF MANIPULATOR

NON-HF MANIPULATOR

NON-HF MANIPULATOR

HF MANIPULATOR

NON-HF MANIPULATOR

HF MANIPULATOR

COMPATIBLE SHEATH + HF MANIPULATOR

NON-HF MANIPULATOR

NON-HF SHEATH +
NON-HF MANIPULATOR

HF SHEATH

HF SHEATH + HF MANIPULATOR

JOINT MECHANISM FOR ENDOSCOPIC TREATMENT INSTRUMENT, AND ENDOSCOPIC TREATMENT SYSTEM USING THAT MECHANISM

BACKGROUND OF THE INVENTION

1. Field of the Invention

The present invention relates to an endoscopic treatment instrument adapted to be passed through a treatment instrument insertion channel of an endoscope, and in particular to a joint mechanism for connection between an manipulating section and a sheath of the endoscopic treatment instrument. The present invention also relates to an endoscopic treatment system using such joint mechanism.

2. Description of Related Art

In general, an endoscopic treatment instrument has a sheath, which is adapted to be inserted through an insertion channel of an endoscope, and a manipulation section for manipulating a treatment tool disposed at a distal end of the sheath. For efficiency in cleansing and disinfection of the instrument and replacement of a damaged sheath, it is desirable to incorporate a joint mechanism that permits the sheath to be separatable from the manipulating section. The joint mechanism should have a simple structure so as not to increase a manufacturing cost.

Japanese Utility Model Kokoku Publication No. Sho. 60-31684 discloses an example of the joint mechanism, in which a plastic member of a joint is split into sub-divisions by the provision of slits, and the sub-divisions are elastically deformed by a fastening ring to connect the sheath to the manipulating section. By loosening the fastening ring, the sheath can be disconnected from the manipulating section.

To achieve complete disinfection or sterilization after use of medical instruments, such medical centers recently increases that use an autoclave (i.e., a high-pressure steam sterilizer). In such medical centers, the treatment instruments are, in many cases, sterilized in a state that the sheath remains connected to the manipulating section.

If the plastic member in an elastically deformed state is subjected to a high-temperature and high-pressure environment of the autoclave, then the plastic member is plastically deformed into the elastically deformed shape, and thus the sheath cannot be disconnected from the manipulating section. In the case where the sheath is left for a long period of time while remaining connected to the manipulating section, the same problem arises.

Accordingly, an object of the present invention is to provide a joint mechanism for an endoscopic treatment instrument, which enables the separation between a sheath and a manipulating section and which is free from the deformation even when the sheath and the manipulating section are left for a long period of time while remaining connected together or when they are subjected to sterilization through use of an autoclave.

An endoscopic treatment system can be constructed using a joint mechanism such that various types of sheaths are provided, each having a respective medical treatment tool at its distal end, and the sheath sections are selectively connected to a common manipulating section according to the treatments required.

The common manipulating section in the above-mentioned endoscopic treatment system is provided with a high frequency power connection terminal to be connected to a high frequency power cord for a high frequency treatment instrument.

Since a metal is exposed on the surface of a sheath of a non-high-frequency (non-HF) treatment instrument, because of the high frequency power cord, the erroneous supply of a high frequency current during the use of the non-HF treatment instrument causes a danger. In general, an assistant prepares a medical treatment instrument, and therefore an accident may arise due to the insufficient communication between the assistant and a surgeon.

If the manipulating section of the high frequency treatment instrument is designed so as to completely preclude compatibility to the sheath of the non-HF treatment instrument, a probability of occurrence of an unforeseeable accident can be eliminated completely.

Even in such a case, a medical treatment instrument which is used both for a high frequency treatment and simply for collecting a tissue sample, e.g., so-called hot biopsy forceps, is used along with a high frequency treatment manipulating section even when the tissue sample is to be collected. There still remains a risk of electrical shock, which would be caused by erroneous application of a high frequency current.

Accordingly, another object of the present invention is to provide an endoscopic treatment system which ensures improved safety by eliminating the risk of electrical shock due to erroneous application of a high frequency current while reducing the number of kinds of manipulating sections.

SUMMARY OF THE INVENTION

To attain the above-noted objects, the present invention provides a joint mechanism for connection between a sheath and a manipulating section of an endoscopic treatment instrument. A joint includes a leading end portion connected to said sheath, and an expanded base end portion having a first cross sectional shape. A receptacle ring is mounted on an leading end portion of said manipulating section and rotatable within a predetermined angular range relative to said leading end portion of said manipulating section. The receptacle ring is formed with an insertion hole having such a second cross section as to permit said expanded base end portion to be passed therethrough. A fitting hole is formed in said leading end portion of said manipulating section so as to non-rotatably receiving said expanded base end portion that has been passed through the insertion hole. By rotating said receptacle ring in a state that said expanded base end portion has been passed through said insertion hole and fitted in said fitting hole, said insertion hole is oriented to inhibit passage of said expanded base end portion therethrough, thereby non-removably connect said joint to said leading end portion of said manipulating section.

The present invention further provides an endoscopic treatment system using a joint mechanism. In the system, an HF manipulating section is provided with a high frequency power connection terminal, whereas a non-HF manipulating section does not have a high frequency power connection terminal. A compatible sheath can be connected to either of the HF manipulating section and the non-HF manipulating section. In contrast, a non-HF sheath can be connected to the non-HF actuation section but cannot be connected to the HF actuation section.

The present disclosure relates to the subject matter contained in Japanese patent application Nos. Hei. 10-6223 (filed on Jan. 16, 1998) and Hei. 10-242630 (filed on Aug. 28, 1998), which are expressly incorporated herein by reference in their entireties.

BRIEF DESCRIPTION OF THE DRAWINGS

FIG. 7 is a perspective view showing the leading end portion of the manipulating section;

DETAILED DESCRIPTION OF THE PREFERRED EMBODIMENTS

Preferred embodiments of the present invention will now be described with reference to the accompanying drawings.

Figure 3:
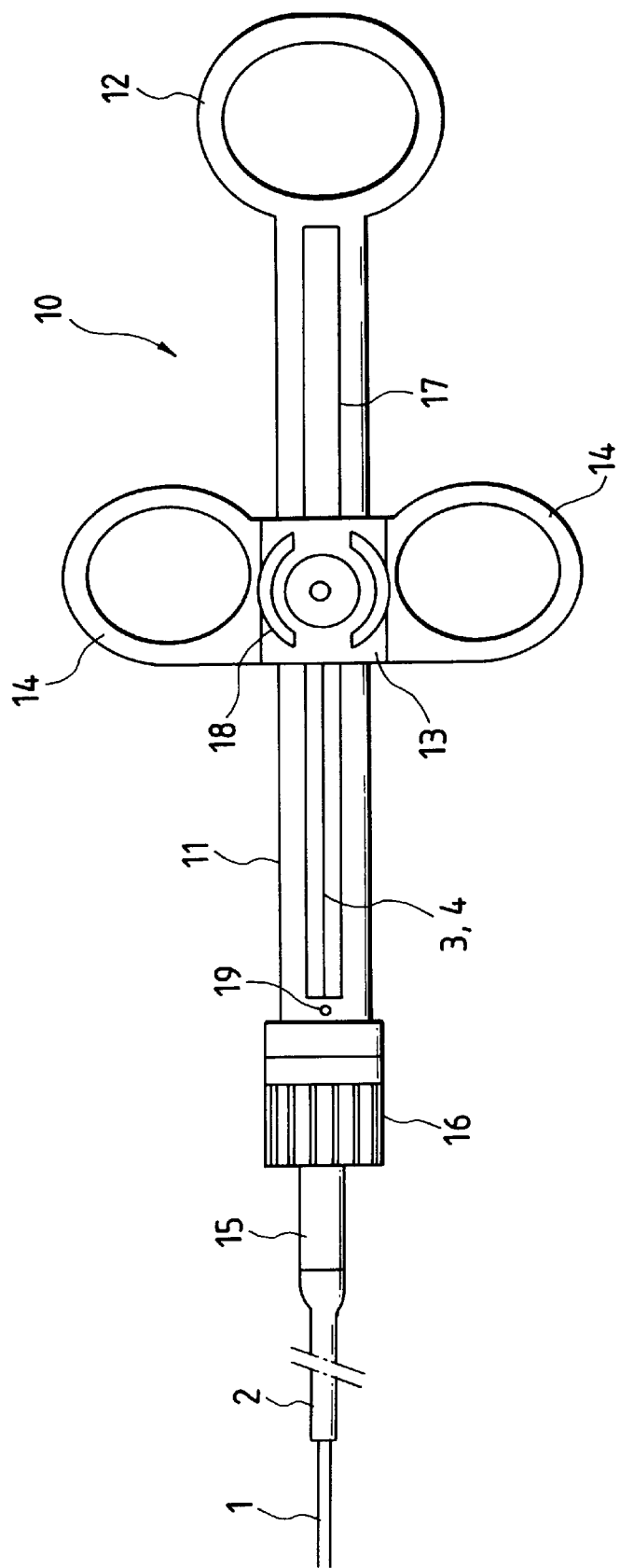
FIG. 3 is a plan view showing the manipulating section.
Figure 4:
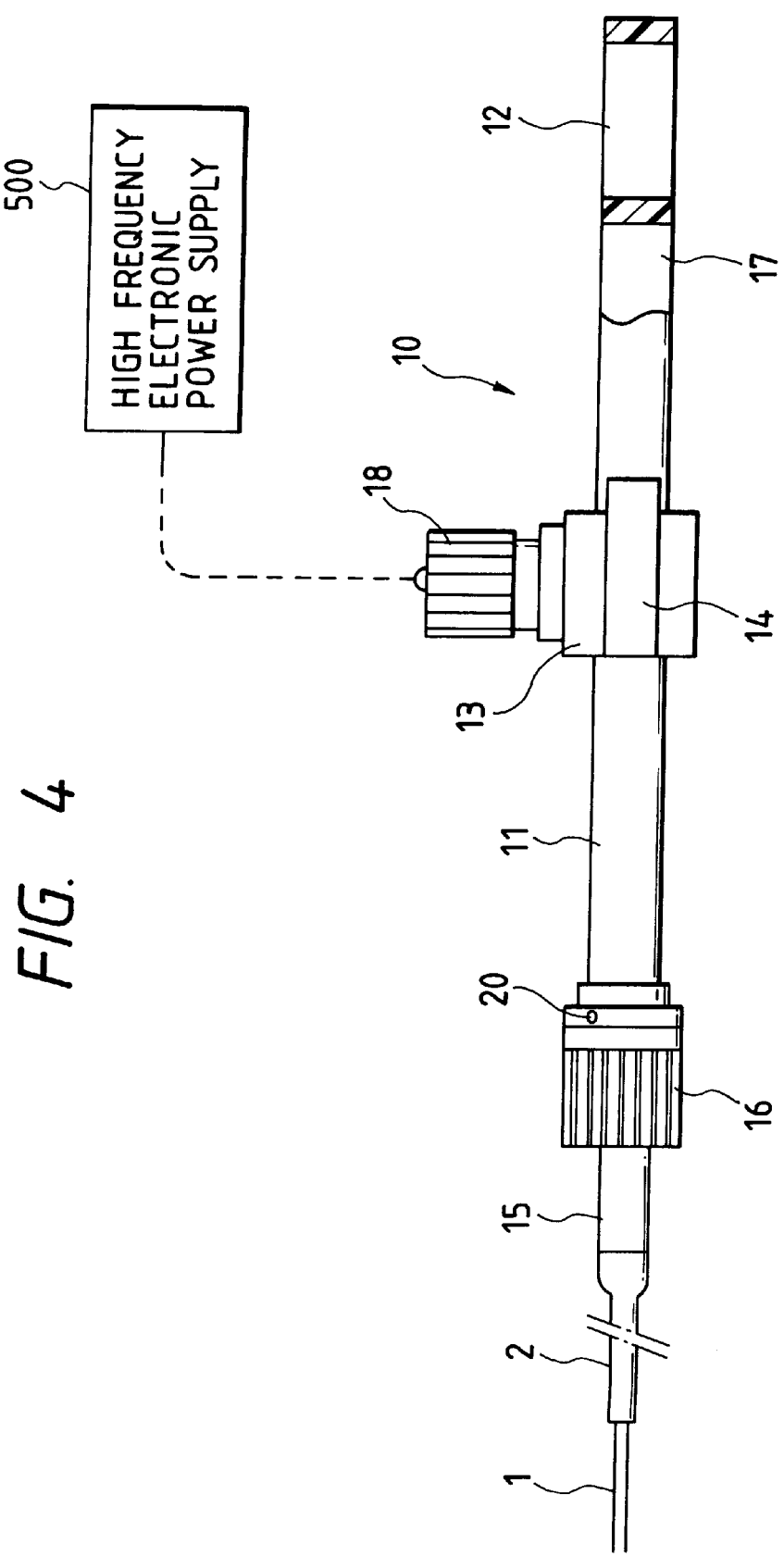
FIG. 4 is a longitudinal side elevation view showing the manipulating section.

FIG. 3 is a plan view showing a manipulating section 10 of an endoscopic treatment instrument. FIG. 4 is a side view showing the manipulating section 10. The manipulating section 10 can be used to manipulate various types of endoscopic treatment instruments, such as a high frequency snare, forceps, etc.

A stationary finger grip 12 is provided at the hand-grip end of an elongated, plastic manipulating section body 11. A movable finger grip 14 for receiving the operator's forefinger and middle finger is provided on a plastic slide member 13 that is mounted on the manipulating section body 11 and that is slidable in a longitudinal direction of the manipulating section body 11.

A sheath 1 is adapted to be inserted into or removed from an insertion channel of an unillustrated endoscope, and the base end of the sheath 1 is connected to the leading end of the manipulating section body 11 through a metal joint 15.

The sheath 1 is constructed by a flexible tube made of, e.g., tetrafluoroethylene. The joint 15 may be made of plastic material, and the sheath 1 may alternatively be made of a metal to form a coiled metal pipe.

Reference numeral 2 designates a buckling prevention tube for preventing the brakage of the sheath 1 as a consequence of being bent sharply. The base end of the crimping prevention tube 2 is attached to the joint 15. Reference numeral 16 designates a plastic receptacle ring for receiving the joint 15 and removably connecting the joint 15 to the leading end of the manipulating section body 11.

The receptacle ring 16 is permitted to rotate in an angular range of 45° about its rotational axis so as to selectively establish either one of a state in which the joint 15 is removable from the manipulating section body 11 and a state in which the joint 15 is non-removably connected to the manipulating section body 11. To allow the user to visually check the angular position of the receptacle ring 16 (i.e., the established state), markers 19 and 20 are assigned to the manipulating section body 11 and the receptacle ring 16, respectively.

An elongated groove 17 is longitudinally formed in the manipulating section body 11. The base end of a manipulating wire 3, which is axially movably inserted into the sheath 1, is connected to the slide member 13 within the groove 17.

Figure 5:
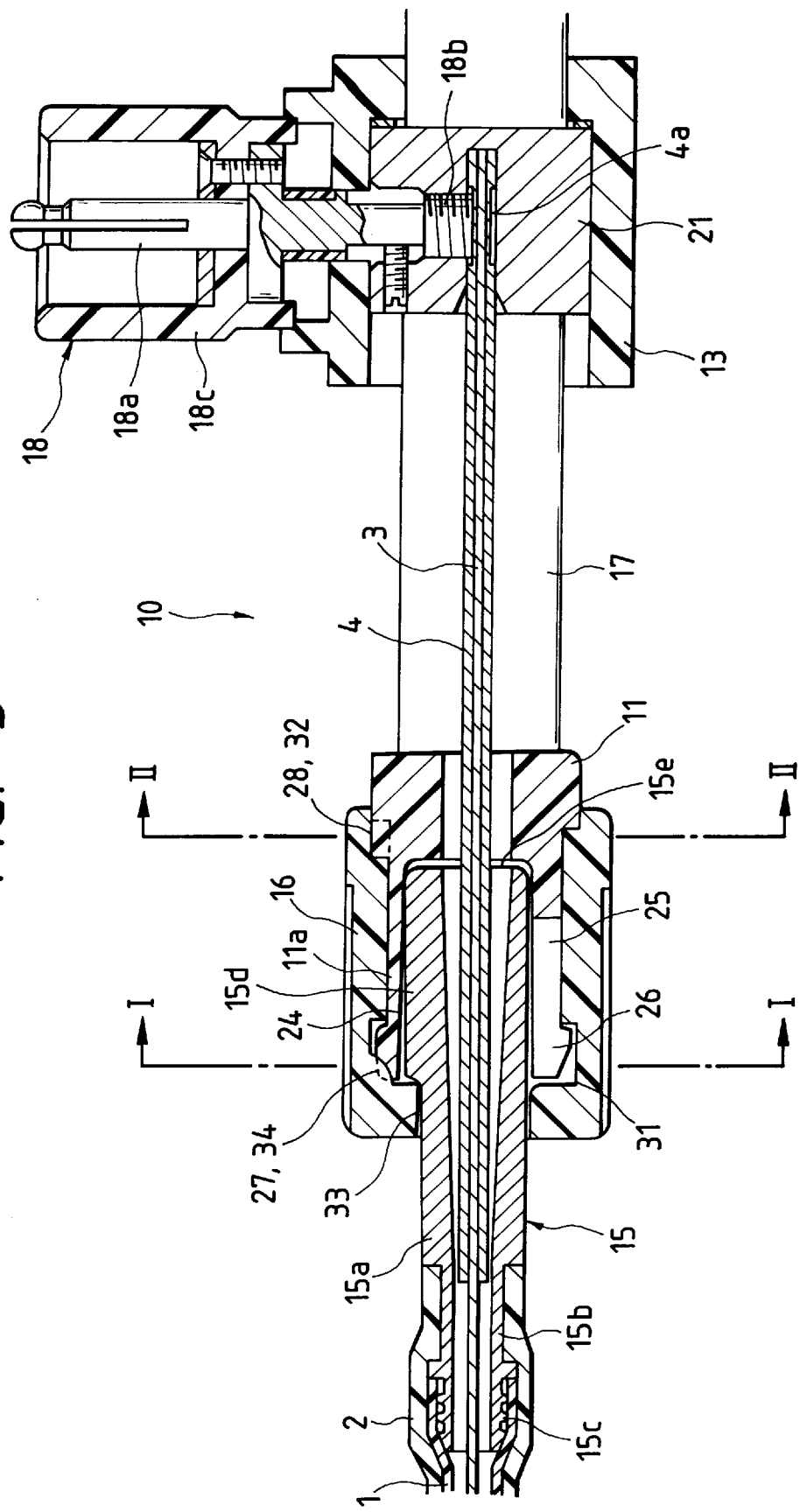
FIG. 5 is a partial side cross-sectional view showing the manipulating section and the sheath.

As best shown in FIG. 5, a metal pipe 4 integrated with the manipulating wire 3 extends along the elongated groove 17 so as to cover the manipulating wire 3 and prevent the buckling of the manipulating wire 3 in the groove 17. Reference numeral 18 designates a high frequency power cord connection terminal provided on the slide member 13, through which a high frequency electric current can be applied to the manipulating wire 3. The metal pipe 4 may be replaced with an electrically insulating plastic tube.

FIG. 5 is a cross-sectional view showing a joint mechanism between the sheath 1 and the manipulating section 10 as well as portions around the slide member 13. An electrically conductive metal connection block 21 is arranged in the groove 17 of the manipulating section body 11. The connection block 21 is fixed to the slide member 13 such that a threaded portion 18b on the root of a contact rod 18a of the connection terminal 18 is screwed into the connection block 21.

The axial end of the threaded portion 18b presses the base end of the manipulating wire 3 and the base end of the metal pipe 4 against the connection block 21. By loosening the threaded portion 18b, the manipulating wire 3 along with the metal pipe 4 can be disengaged from the connection block 21.

A constricted portion 4a is formed in the area of the metal pipe 4 that is brought into contact with the axial end of the threaded portion 18b. The provision of the constricted portion 4a avoids the removal of the metal pipe 4 from the connection block 21 due to the unintentional slight loosening of the threaded portion 18b.

The contact rod 18a is protruded from the slide member 13, and a plastic receiving tube 18c is fixed to the slide member 13 by a screw so as to circumscribe the protruded contact rod 18a. An unillustrated connector of a high frequency power cord can be connected to the contact rod 18a.

Figure 6:
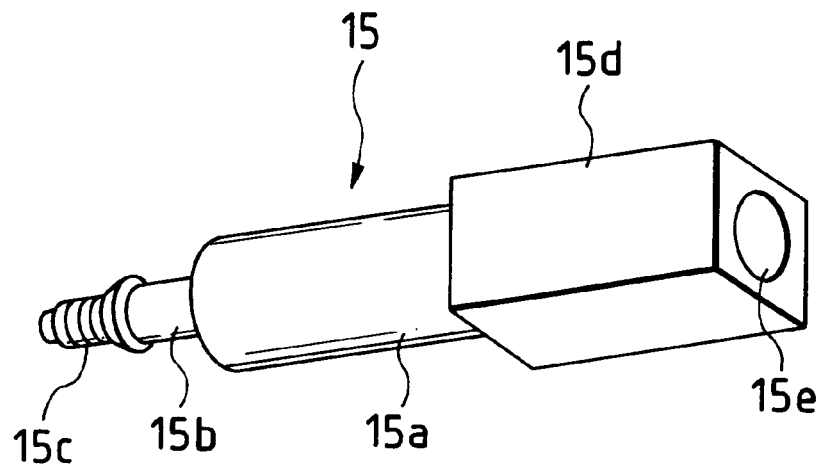
FIG. 6 is a perspective view showing the joint of the sheath.

As shown in FIG. 6, the joint 15 includes a cylindrical intermediate portion 15a, a buckling prevention tube connection portion 15b on the leading-side of the cylindrical intermediate portion 15a, and the sheath connection portion 15c on the leading-side of the buckling prevention tube connection portion 15b. The base end of the crimping prevention tube 2 is press-fitted onto the buckling prevention tube connection portion 15b smaller in diameter than the cylindrical intermediate portion 15a. The base end of the sheath 1 is press-fitted onto the sheath connection portion 15c smaller in diameter than the buckling prevention tube connection portion 15b. The outer circumferential surface of the sheath connection section 15c is formed into corrugations that are tapered and wedged to prevent the removal of the sheath 1 therefrom.

The joint 15 further includes a square cross-sectional section 15d extending from the base-end side of the intermediate portion 15a. The square cross-sectional section 15d is substantially square in cross section so that the four corners of this section 15d project radially outwardly from the outer surface of the intermediate portion 15a. As shown in FIG. 6, the intermediate portion 15a forms a constricted portion of the joint 15, and the section 15d forms an expanded portion of the joint 15.

A tapered hole 15e is axially passed through the joint 15 to dispose the manipulating wire 3 and the metal pipe 4 therealong. The tapered hole 15e has a maximum diameter at its base-end side opening, and the diameter of the tapered hole 15e is gradually reduced as it approaches the distal-end side opening.

The tapered configuration of the hole 15e is analogous to a so-called cone angle (shape) of a syringe, and therefore, after a clinical operation with the endoscopic treatment instrument, a syringe filled with a cleansing liquid can be readily connected to cleanse the inside of the sheath 1.

As shown in FIG. 7, the leading end side of the manipulating section body 11 is substantially cylindrical (i.e. a hollow circular in cross section). A fitting hole 24 square in cross section axially extends from the leading end of the manipulating section body 11 so that the square cross-sectional section 15d of the joint 15 can be fitted into the fitting hole 24.

The leading end side of the manipulating section body 11 is divided into four split pieces 11a by diagonally arranged four slits 25. The slits 25 extend in parallel to the axis of the manipulating section body 11 from the leading end of the manipulating section body 11 up to the vicinity of the bottom of the fitting hole 24, so that each of the individual split pieces 11a can be elastically deformed, like a leaf spring, in the direction orthogonal to the axis of the manipulating section body 11.

The leading end of the manipulating section body 11 is expanded radially outwardly similar to the head of a mushroom to have a large-diameter portion 26. The large-diameter portion 26 is tapered in the leading-end direction. A single protrusion 27 for clicking engagement is provided on the tapered surface of the large-diameter portion 26.

The protrusion 27 is formed into a round shape. A rectangular stopper protrusion 28 is formed on the outer surface of the manipulating section body 11 at a position spaced a short distance away from the large-diameter portion 26.

As shown in FIG. 5, the receptacle ring 16 is fitted around the leading end side of the manipulating section body 11. The receptacle ring 16 is a cylindrical cap which is loosely contacted with the outer surfaces of the split pieces 11a of the manipulating section body 11. Further, an annular recess 31 is formed in the interior of the receptacle ring 16 to define a larger-inner-diameter portion, which accommodates the large-diameter portion 26 of the manipulating section body 11.

In order to fit the receptacle ring 16 to the manipulating section body 11, the leading end portion of the manipulating section body 11 is inserted into the receptacle ring 16. During the course of insertion of the manipulating section body 11 into the receptacle ring 16, the split pieces 11a of the manipulating section body 11 are elastically deformed inwardly until the large-diameter portion 26 of the manipulating section body 11 reaches the annular recess 31 of the receptacle ring 16. That is, after the large-diameter portion 26 reaches the recessed portion 31 and thus is accommodated therein, the split pieces 11a return to their original states in which no elastic deformation is caused.

As shown in FIG. 5, when the receptacle ring 16 is completely fitted around the leading end portion of the manipulating section body 11, the receptacle ring 16 is permitted to rotate relative to the manipulating section body 11 but retained axially by the large-diameter portion 26 of the manipulating section body 11.

Figure 2:
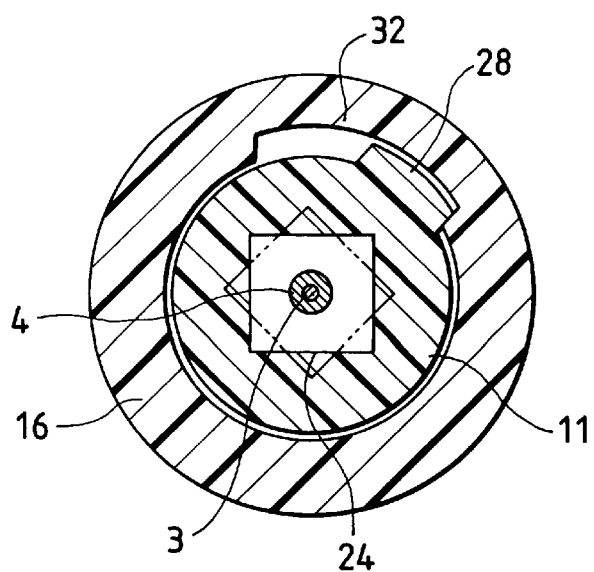
FIG. 2 is a cross-sectional view taken along line II—II of FIG. 5, showing a receptacle ring fitted around the manipulating section.

As shown in FIG. 2 which is a cross-sectional view taken along line II—II of FIG. 5, a fan-shaped space 32 is formed along the interior surface of the receptacle ring 16 for restricting the rotation of the receptacle ring 16 to an angle of, for instance, 45° in cooperation with the stopper protrusion 28 of the manipulating section body 11.

Figure 1A:
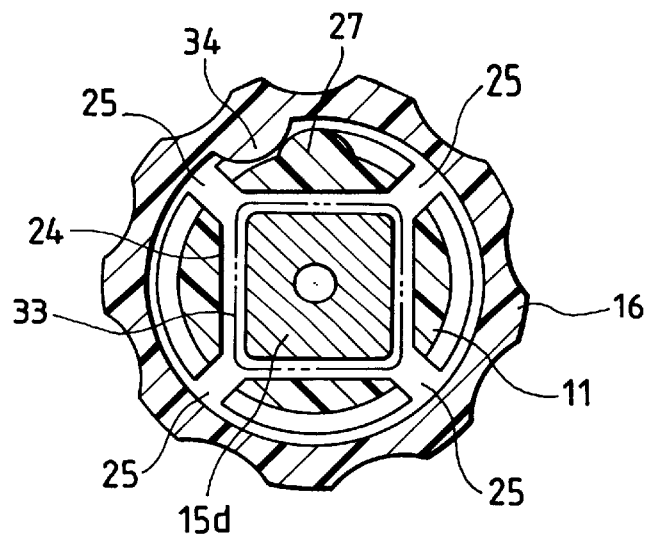
FIGS. 1A and 1B are cross-sectional views taken along line I—I of FIG. 5, showing a joint of a sheath, and a manipulating section in a joint mechanism according to an embodiment.
Figure 1B:
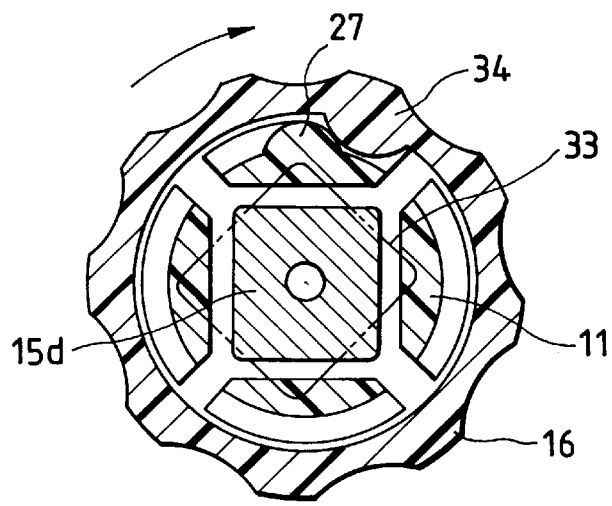

Further, as shown in FIGS. 1A and 1B which are cross-sectional views taken along line I—I of FIG. 5, a protrusion 34 is provided to project inwardly from the interior surface of the receptacle ring 16 and cooperate with the protrusion 27 on the leading end of the manipulating section body 11. The protrusion 34 and the protrusion 27 provides a click engagement, which inhibits the undesired rotation of the receptacle ring 16 relative to the manipulating section body 11 within an angular range (for instance, 45°) defined by stopper protrusion 28 and the space 32. In addition, the actuation wire 3 and the metal pipe 4 are omitted in FIGS. 1A and 1B.

Figure 8:
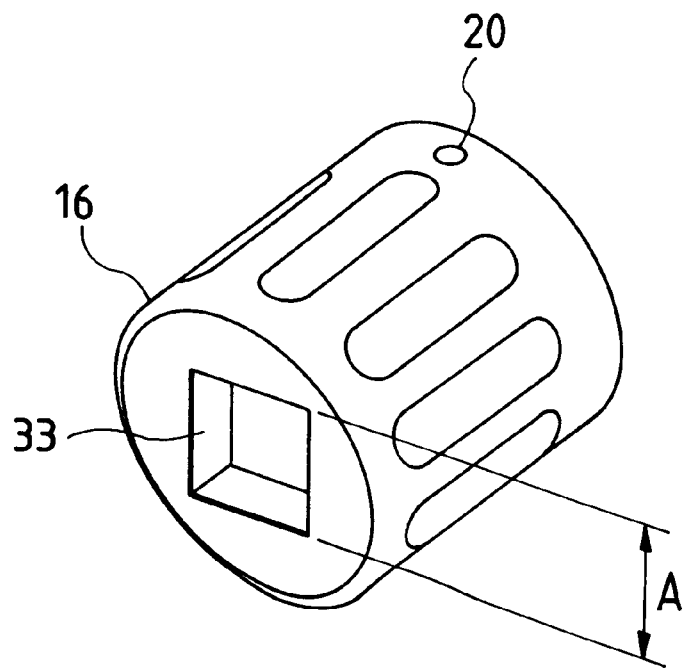
FIG. 8 is a perspective view showing the receptacle ring.

As shown in FIG. 8, the receptacle ring 16 is formed with a rectangular hole 33. The rectangular hole 33 is provided on the leading end face of the receptacle ring 16, and aligned on the rotational axis of the receptacle ring 16. The rectangular hole 33 has a rectangular shape slightly larger than the rectangular shape of the rectangular cross-sectional portion 15*d* of the joint 15. The length A of the section line of the rectangular hole 33 is equal to or larger than the outer diameter of the intermediate portion 15*a* of the joint 15 but smaller than the length of the diagonal line of the rectangular cross-sectional portion 15*d* of the joint 15.

As shown in FIG. 1A, if the rectangular hole 33 of the receptacle ring 16 is positioned in conformity with the fitting hole 24 of the manipulating section body 11, the rectangular cross-sectional section 15*d* of the joint 15 can be fitted into or removed from the fitting hole 24 through the rectangular hole 33.

On the other hand, as shown in FIG. 1B, if the receptacle ring 16 is rotated by 45° to offset the rectangular hole 33 of the receptacle ring 16 with respect to the fitting hole 24 of the manipulating section body 11, the rectangular cross-sectional portion 15*d* cannot be fitted into or removed from the fitting hole 24 through the rectangular hole 33.

In this way, the sheath 1 can be arbitrarily connected to or removed from the manipulating section 10. During the travel of the protrusion 34 in association with the rotation of the receptacle ring 16, the protrusion 34 interferes with the protrusions 27 at positions other than ends of the range of rotation of the receptacle ring 16.

More specifically, when the press ring 16 is rotated, the inwardly directed protrusion 34 depresses the outwardly directed protrusion 27 so as to elastically and inwardly deform the split piece 11*a* of the manipulating section body 11 through the protrusion 27, and then the protrusion 34 passes across the protrusion 27 to reach one of the ends of the rotational range, whereby the split piece 11*a* returns to its original state. That is, no member is elastically deformed when the protrusion 27 reaches either one of the ends of the rotational range.

Accordingly, although there is a need to apply at least a certain degree of force in order to rotate the receptacle ring 16 from one of the ends of the rotational range to the other, the receptacle ring 16 is held in place in a stable manner once the receptacle ring 16 is positioned at either of the ends of rotational range. In addition, since each of the protrusions 27 and 34 is designed to have an arcuate contacting surface, the receptacle ring 16 does not stay in the rotation midway (i.e., at positions other than the ends of rotational range) where the protrusions 27 and 34 are in contact with each other while receiving an elastic restoring pressure.

As shown in FIG. 1B, in the condition in which the joint 15 is non-removably connected to the manipulating section body 11, no member exerts force on any other members, and all the members remain in their original states.

Therefore, even if the sheath 1 is left for a long period of time or subjected to sterilization in an autoclave while remaining connected to the manipulating section 10, any members of the sheath 1 and the manipulating section 10 will not become deformed, thereby maintaining superior operability.

Figure 9:
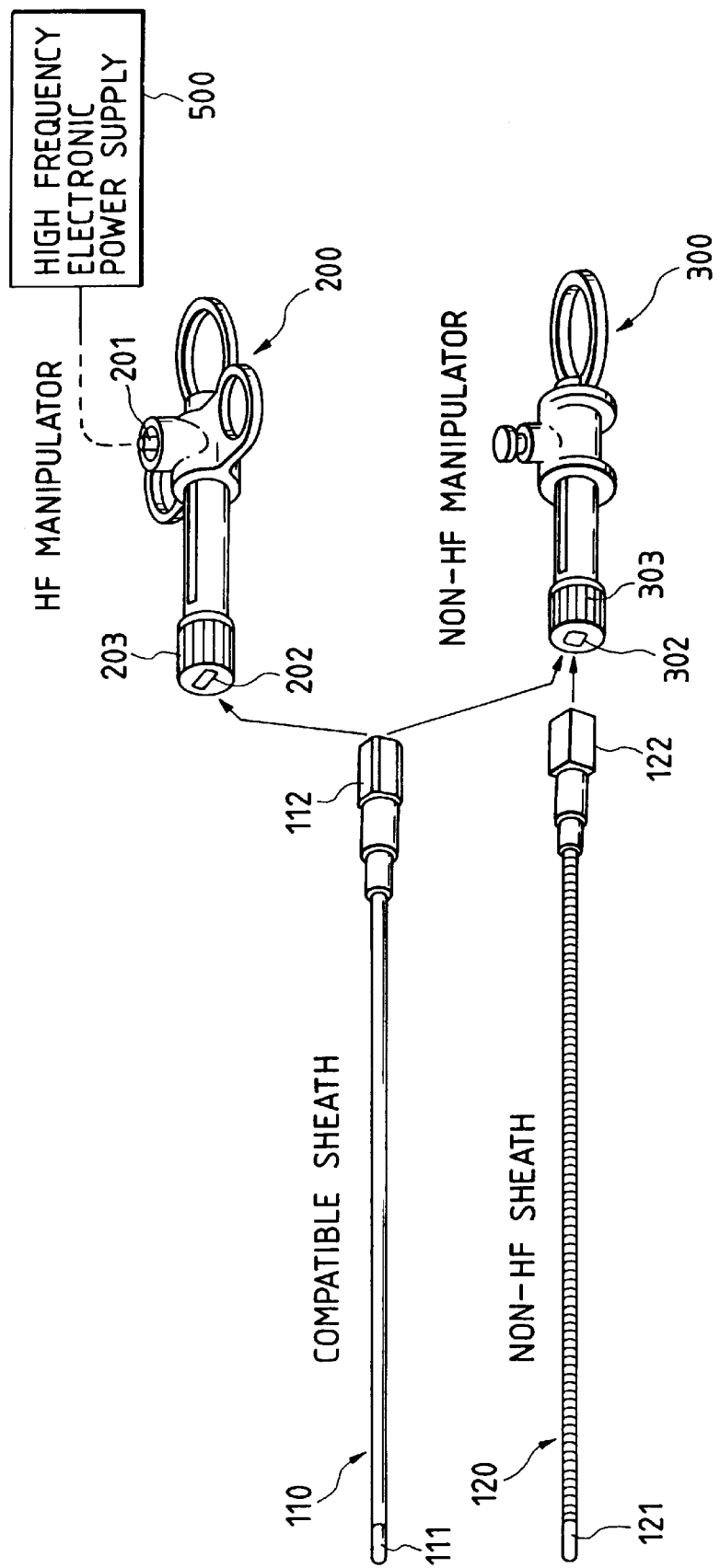
FIG. 9 is a perspective view showing an endoscopic treatment system using a joint mechanism according to another embodiment.

FIG. 9 shows an endoscopic treatment system using a joint mechanism, which includes sheaths 110, 120 provided at their leading ends with treatment members 111, 121 and adapted to be inserted into a treatment tool insertion channel of an endoscope, and manipulating sections 200, 300 adapted to be removably connected to the base ends of the sheaths 110, 120 in order to remotely manipulate the treatment members 111, 121.

The system is provided with two types of manipulating sections, i.e. the manipulating section 200 for high frequency treatment (hereinafter referred to simply as a "HF manipulating section") having a high frequency power connection terminal 201, and the manipulating section 300 for non-high-frequency treatment (hereinafter referred to simply as a "non-HF manipulating section") having no high frequency power connection terminal. In addition, the HF manipulating section (the HF sheath) used herein means a manipulating section (a sheath) that is designed to lead a high frequency current from a high-frequency electric power supply to the leading end of a sheath for electric cauterization.

Further, the system is provided with two types of sheaths, i.e. the sheath 110 (hereinafter referred to simply as a "compatible sheath") which can be connected to either of the HF manipulating section 200 and the non-HF manipulating section 300, and the sheath 120 dedicated for non-HF treatment(hereinafter referred to as a "non-HF sheath") which can be connected to the non-HF manipulating section 300 but not to the HF manipulating section 200.

The exposed outer surface of the non-HF sheath 120 is constructed by a conductive member, such as a coiled pipe made by tightly coiling a stainless steel wire to a predetermined diameter. The non-HF sheath 120 constitutes, for instance, a biopsy forceps, a three-claw gripping forceps, or a basket.

The compatible sheath 110 constitutes, for instance, a hot biopsy forceps, a snare for removing a polypectomy snare, or a basket, and is characterized in that the outer surface of the compatible sheath 110 is covered with an electrically insulating member, such as a tube made of tetrafluoroethylene. A tightly-wrapped coiled pipe may be or may not be provided inside the electrical insulating tube of the compatible sheath 110.

Joints 112, 122 have joint portions (corresponding to the square-cross sectional portion 15*d* in the joint mechanism described with reference to FIGS. 1 to 8) that are thicker than the rests of the joints 112, 122 for connection to the manipulating sections 200, 300, and are attached to the base ends of the sheaths 110, 120. Receptacle rings 203, 303 are attached to the tip ends of the manipulating sections 200, 300, and have insertion holes 202, 302 which selectively permit the insertion of the joints 112, 122 thereinto.

The compatible joint 112 attached to the base end of the compatible sheath 110 is insertable into either one of the HF insertion hole 202 and the non-HF insertion hole 302. Accordingly, the compatible sheath 110 can be connected to either one of the HF manipulating section 200 and the non-HF manipulating section 300.

In contrast, the non-HF joint 122 attached to the base end of the non-HF sheath 120 is insertable into the non-HF insertion hole 302 but is not insertable into the HF insertion hole 202. Accordingly, the non-HF sheath 120 can be connected to the non-HF manipulating section 300 but cannot be connected to the HF manipulating section 200. Details of the joint mechanism in this system will be described later.

Figure 10:
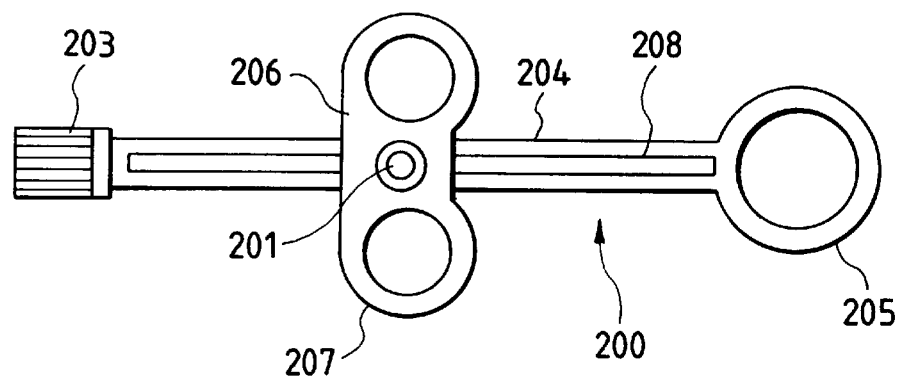
FIG. 10 is a plan view showing an HF manipulating section.

FIG. 10 shows the HF manipulating section 200. A manipulating section body 204 is formed from electrically insulating plastic into an elongated rod-like shape, and an annular first finger grip 205 is provided at the end of the manipulating section body 204 so as to receive operator's thumb. An elongated slit 208 is extended longitudinally over the entire length of the manipulating section body 204.

Reference numeral 206 designates a slider that is formed from electrically insulating plastic and that is mounted axially slidably on the manipulating section body 204. The slider 206 has second finger grips 207 for receiving operator's forefinger and middle finger. A high frequency power connection terminal 201 is also provided on the slider 206.

Figure 11:
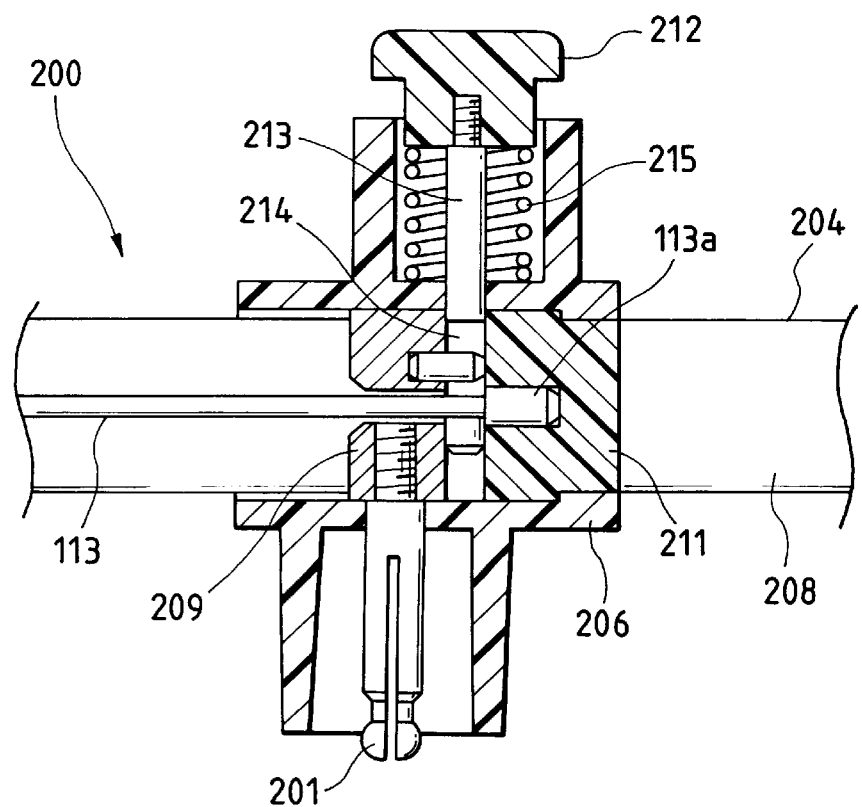
FIG. 11 is a partial side-cross-sectional view showing the HF manipulating section.

FIG. 11 shows a portion of the HF manipulating section, where the slider 206 is mounted on the manipulating section body 204. Reference numeral 113 designates a manipulating wire that is protruded from the base end of the sheath 110 to be manipulated through the manipulating section 200. A stopper 113a is formed at the end of the manipulating wire 113, which is larger in outer diameter than the manipulating wire 113.

Reference numeral 211 designates an electrical insulating block held by the slider 206 within the slit 208. The stopper 113a is inserted into a blind hole formed in the electrical insulating block 211.

Reference numeral 212 designates a manipulating wire release button for locking or releasing the base end of the manipulating wire 113 to or from the slider 206. A slide shaft 213 is attached coaxially to the manipulating wire release button 212. A slit 214 of the narrowest possible width is formed through the slide shaft 213 so as to permit the passage of the stopper 113a of the manipulating wire 113 therethrough.

The manipulating wire release button 212 is biased outwardly by the action of a compression coil spring 215. When the manipulating wire release button 212 is pushed inwardly against the biasing force of the compression coil spring 215, the slide shaft 213 is set in such a position that the stopper 113a can pass through the slit 214, and thus the engagement/disengagement of the stopper 113a of the manipulating wire 113 with/from the slider 206 is possible.

As shown in FIG. 11, if the operator's finger is released from the manipulating wire release button 212, the biasing force of the compression coil spring 215 sets and maintains the slide shaft 213 in such a position as to inhibit the stopper 113a from passing through the slit 214, and therefore the stopper 113a of the manipulating wire 113 is fixed to the slider 206.

The manipulation of the slider 206 back and forth in the foregoing state causes the actuation wire 113 to be moved back and forth, thereby enabling remote manipulation of the treatment member 111 provided at the leading end of the sheath 110.

The high frequency power connection terminal 201 is screwed into a terminal receiving member 209 made of conductive metal. An unillustrated high frequency power cord is connected to the high frequency power connection terminal 201, thereby enabling application of a high frequency electric current to the treatment member 111 through the terminal receiving member 209, the slide shaft 213, and the manipulating wire 113.

Figure 12:
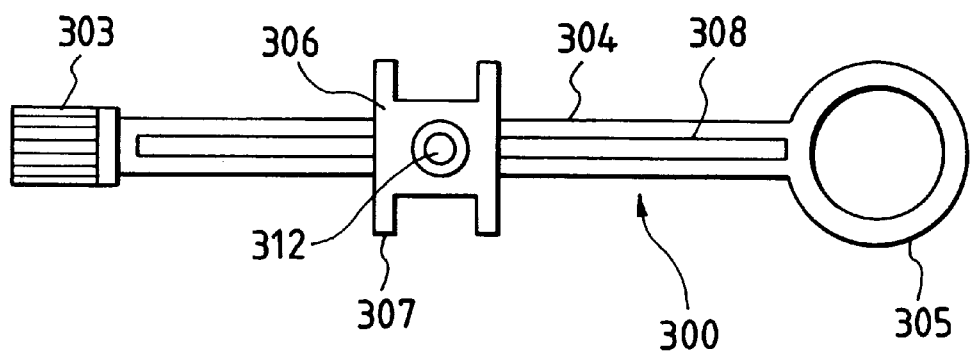
FIG. 12 is a plan view showing a non-HF manipulating section.

FIG. 12 shows the non-HF manipulating section 300 which includes a manipulating section body 304, a first finger grip 305, a slit 308 and so on similar to the HF manipulating section 200. A second finger grip 307 is formed into a spool-like shape so that the operator or the like can visually distinguish the non-HF manipulating section 300 from the HF manipulating section 200. Reference numeral 312 designates a manipulating wire release button.

Figure 13:
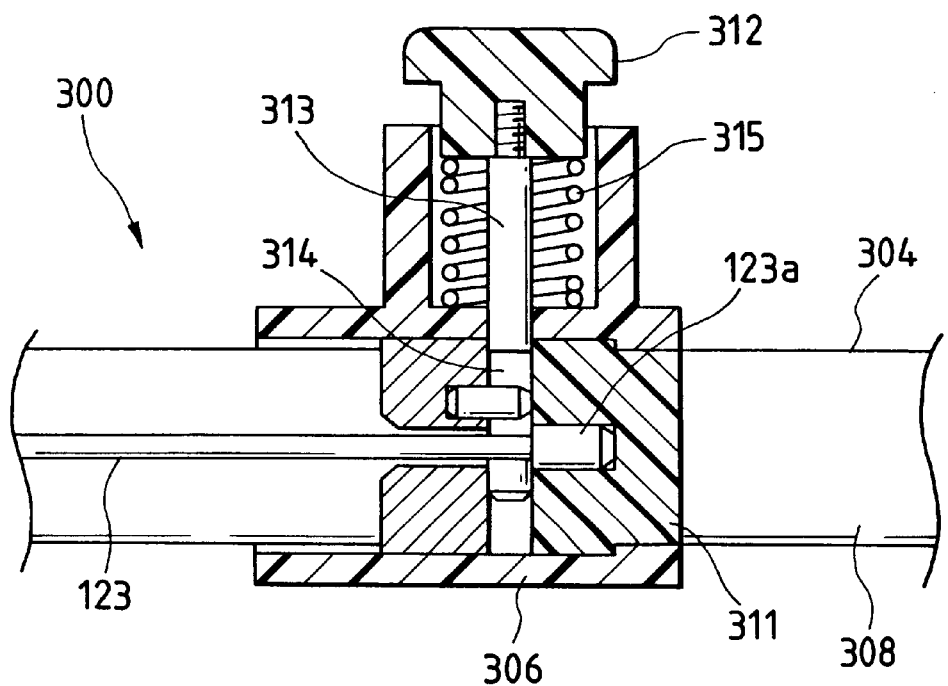
FIG. 13 is a partial side-cross-sectional view showing the non-HF actuation section.

FIG. 13 shows a portion of the non-HF manipulating section 300 where the slider 306 is mounted on the manipulating section body 304. This portion of the non-HF manipulating section 300 is identical in structure to that of the high frequency manipulating section 200, except that the non-HF manipulating section 300 does not have a high frequency power connection terminal. Reference numeral 311 designates an electrically insulating block; 313 designates a slide shaft; 314 designates a slit; and 315 designates a compression coil spring.

Figure 14:
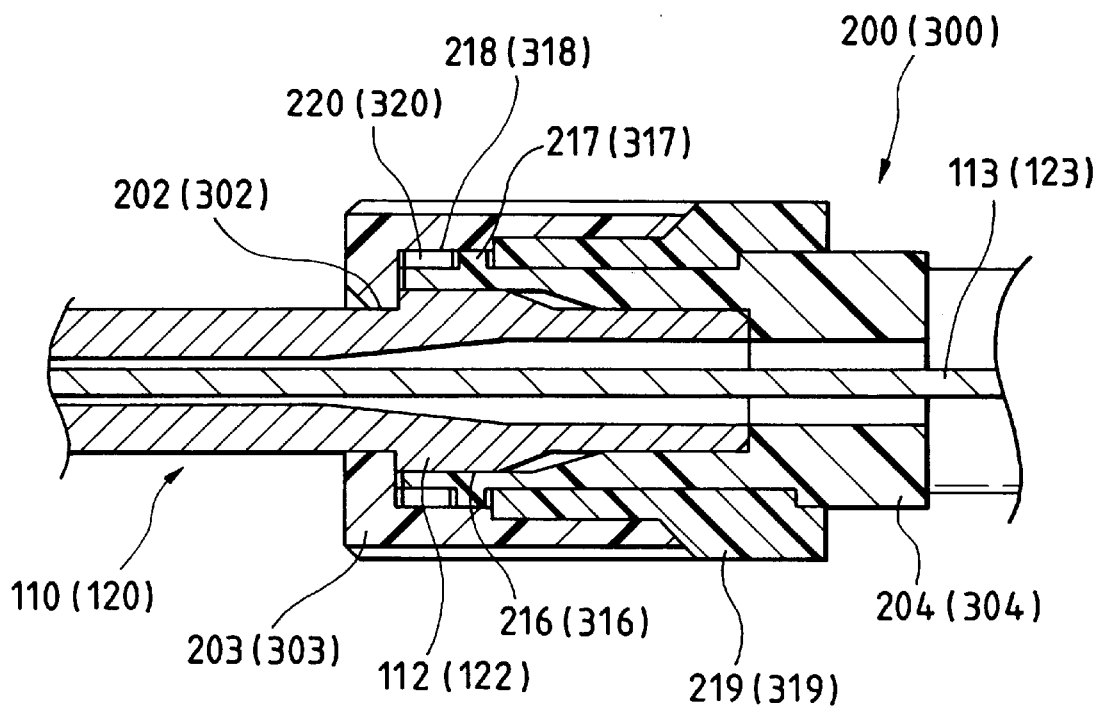
FIG. 14 is a side cross-sectional view showing the joint mechanism between the manipulating section and the sheath.
Figure 15:
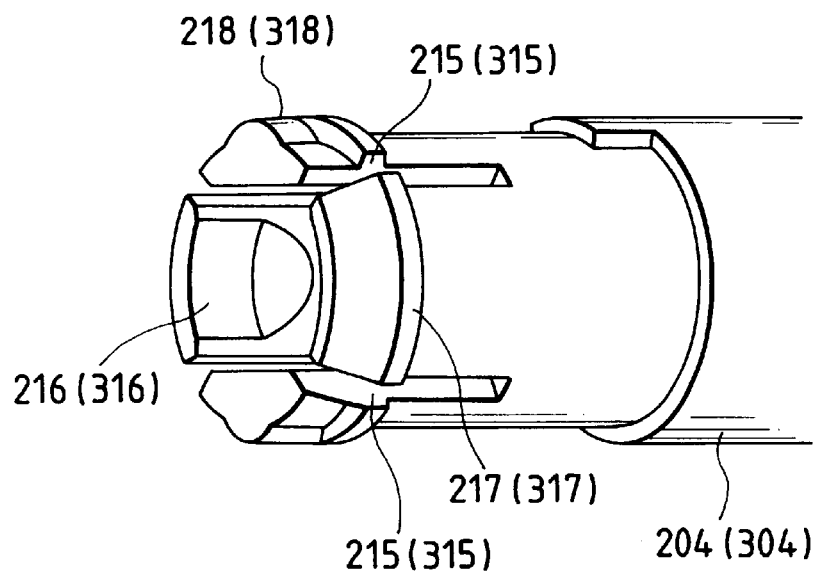
FIG. 15 is a perspective view showing the leading end of the manipulating section.

FIG. 14 shows the joint portion where the sheath 110 (120) is connected to the manipulating section 200 (300). FIG. 15 shows the leading end of the manipulating section body 204 (304) to which the sheath 110 (120) is to be connected.

The leading end of the manipulating section body 204 (304) is split into four segments by four slits 215 (315) extending from the leading end side of the manipulating section body 204 (304). The four slits 215 (315) are spaced at predetermined angular intervals, for instance 90°. A joint insertion hole 216 (316) is defined inside the four segments, which can receive either of the joints 112 and 122 of the sheath 110 and 120.

A circumferential protrusion 217 (317) is formed at a position spaced a short distance away from the leading end surface of the manipulating section body 204 (304). As shown in FIG. 14, an engagement cylinder 219 (319) is fitted on the manipulating section body 204 (304) behind the circumferential protrusion 217 (317), so that the circumferential protrusion 217 (317) prevents the removal of the engagement cylinder 219 (319).

The receptacle ring 203 (303) is engaged with the engagement cylinder 219 (319) so as to be axially retained on the end of the manipulating section 200 (300). The engagement structure using the annular recess 31 and the large-diameter portion 26 described in connection with FIGS. 1 to 8 can be utilized for engagement between the receptacle ring 203 (303) and the engagement cylinder 219 (319). When the receptacle ring 203 (303), the engagement cylinder 219 (319) and the manipulating section body 204 (304) are coupled together completely, no elastic deformation is caused in these components.

The receptacle ring 203 (or 303) is rotatable about its axis within a rotational range, for instance, 45°. A pair of clicking protrusions 220 (320) are formed on the internal circumference of the rotatable receptacle ring 203 (303), whereas a pair of clicking protrusions 218 (318) are formed on the outer circumference of the stationary manipulating section body 204 (304). Therefore, the receptacle ring 203 (303) is stopped and retained at either one of the ends of the rotational range after the clicking protrusions 220 (320) have passed across the clicking protrusions 218 (318).

Figure 16:
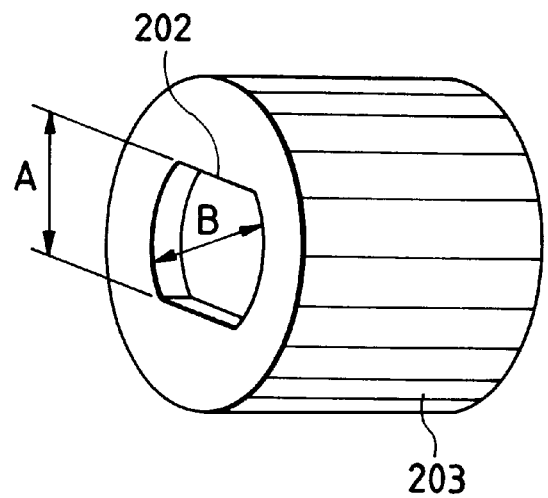
FIG. 16 is a perspective view showing an HF receptacle ring.
Figure 17:
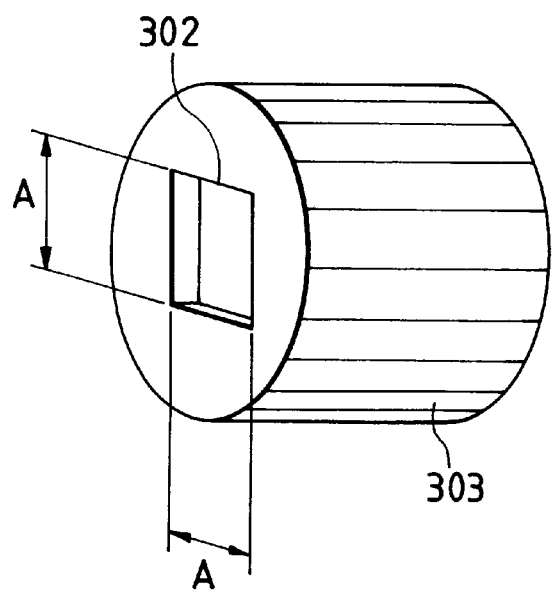
FIG. 17 is a perspective view showing a non-HF receptacle ring.

As shown in FIG. 16, the HF insertion hole 202 formed in the HF receptacle ring 203 has an oblong shape having a width A and a major diameter B. In contrast, as shown in FIG. 17, the non-HF insertion hole 302 formed in the non-HF receptacle ring 303 has a regular square shape whose side is A.

Figure 18:
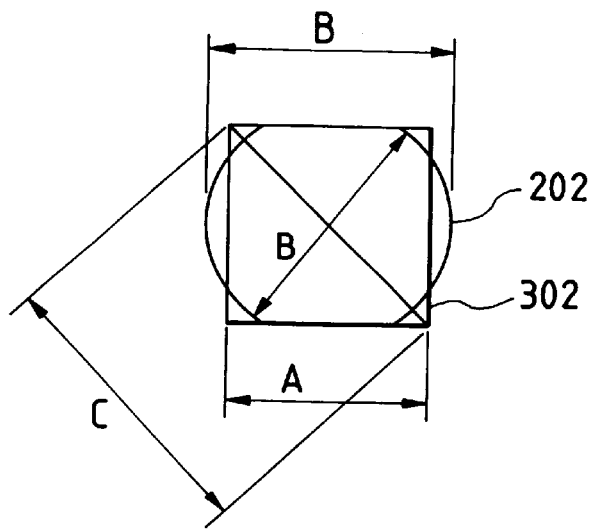
FIG. 18 is a schematic representation showing a dimensional relationship between an HF insertion hole of the HF receptacle ring and a non-HF insertion hole of the non-HF receptacle ring.

It is preferable that the relationship between A and B is expressed by A<B<1.4A, and more preferably, 1.2A<B<1.3A. As shown in FIG. 18, the major diameter B of the oblong HF insertion hole 202 is larger than the length A of the opposite side of the regular square non-HF insertion hole 302, and smaller than the length C of the diagonal line of the regular square non-HF insertion hole.

Figure 19:
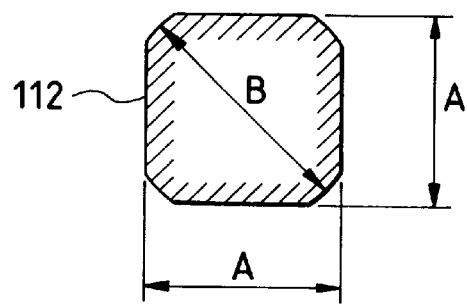
FIG. 19 is a cross-sectional view taken along a plane perpendicular to the axis of a compatible joint.

As shown in FIG. 19, the joint 112 of the compatible sheath 110 has such a cross section shape that four corners of a regular square whose side is A are rounded or chamfered to have the diameter B. Accordingly, the joint 112 can be inserted into either one of the HF insertion hole 202 and the non-HF insertion hole 302.

Figure 20:
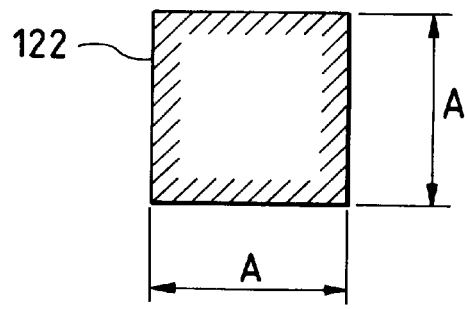
FIG. 20 is a cross sectional view taken along a plane perpendicular to the axis of a non-HF joint.

As shown in FIG. 20, the non-HF joint 122 of the non-HF sheath 120 has a regular square cross section shape whose side is A. Consequently, the non-HF joint 122 cannot be inserted into the HF insertion hole 202 but can be inserted into the non-HF insertion hole 302.

The dimensions A and B of the holes are held to have positive tolerances, whereas the dimensions A and B of the joints are held to have negative tolerances (the same applies to the aforementioned and following description). Accordingly, a joint having dimension A passes through a hole having dimension A, and a joint having dimension B passes through a hole having dimension B.

Figure 21:
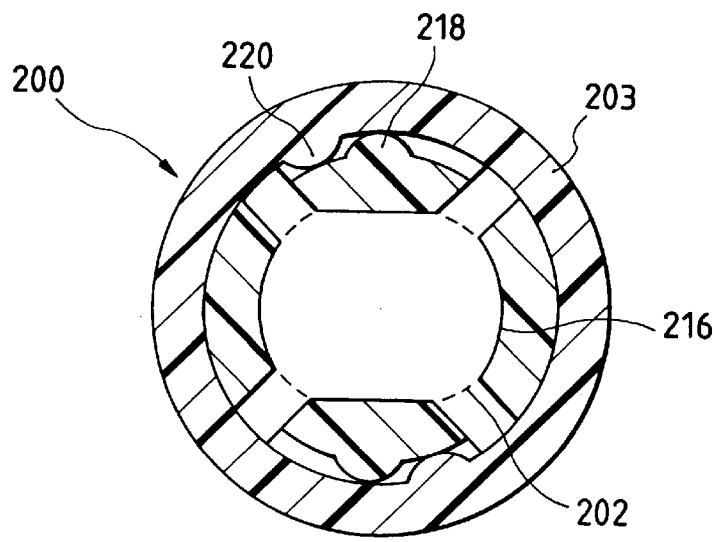
FIG. 21 is a cross sectional view taken along a plane perpendicular to the axis of the leading end of the HF manipulating section.

FIG. 21 is a cross-sectional view taken along a plane perpendicular to the axis of the leading end of the HF manipulating section 200. The cross section of the insertion hole 216 matches with that of the HF insertion hole 202 designated by a two-dot chain line. Consequently, the joint 112 that can be inserted into the HF insertion hole 202 can be fitted into the insertion hole 216.

Figure 22:
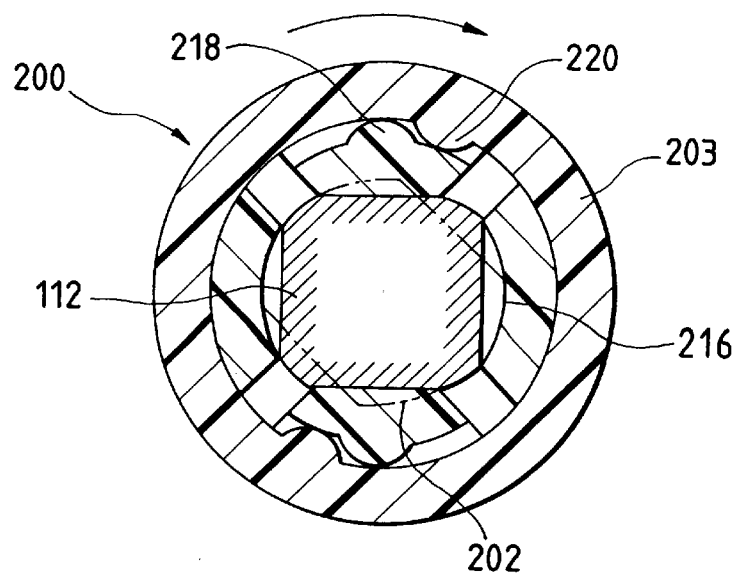
FIG. 22 is a cross-sectional view taken along a plane perpendicular to the axis of the joint, showing a state in which the compatible sheath is connected to the HF manipulating section.

FIG. 22 shows a state in which the HF receptacle ring 203 is rotated by 45° until the clicking protrusions 220 has passed across the clicking protrusions 218 after the joint 112 has been fitted through the HF insertion hole 202 into the insertion hole 216. As illustrated, since the HF insertion hole 202 is also rotated, the joint 112 is not removable from the inside of the mouthpiece insertion hole 216, and thus the compatible sheath 110 is connected to the HF manipulating section 200.

So long as the HF receptacle ring 203 is reversely rotated until it returns to its original position shown in FIG. 21, the joint 112 can be removed from the insertion hole 216 to disconnect the compatible sheath 110 from the HF manipulating section 200.

Figure 23:
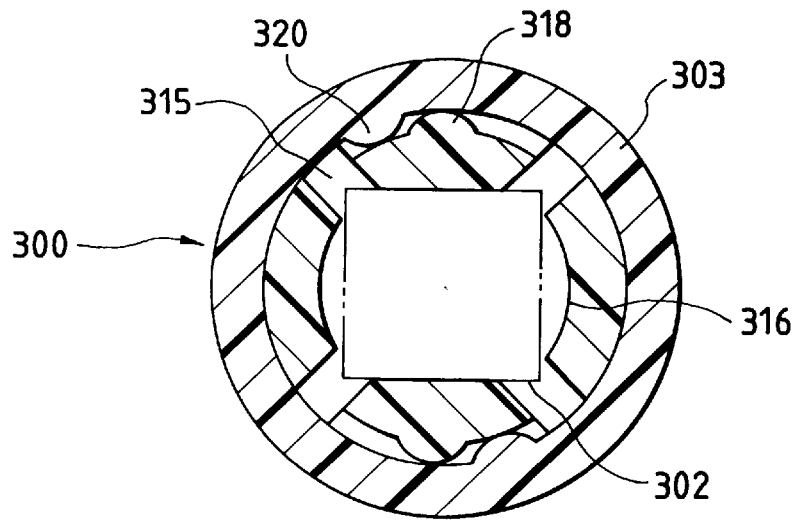
FIG. 23 is a cross-sectional view taken along a plane perpendicular to the axis of the leading end of the non-HF manipulating section.

FIG. 23 is a cross-sectional view taken along plane which is perpendicular to the axis of the leading end of the non-HF manipulating section 300. The cross sectional shape of the insertion hole 316 is the same as that of the insertion hole 216 of the HF manipulating section 200. Since the slits 315 form spaces corresponding to the corners of the non-HF insertion hole 302, the joint that can be inserted into the non-HF insertion hole 302 can be fitted into the insertion hole 316. Reference numerals 318 and 320 designate clicking protrusions on the stationary and rotatable sides, respectively.

Figure 24:
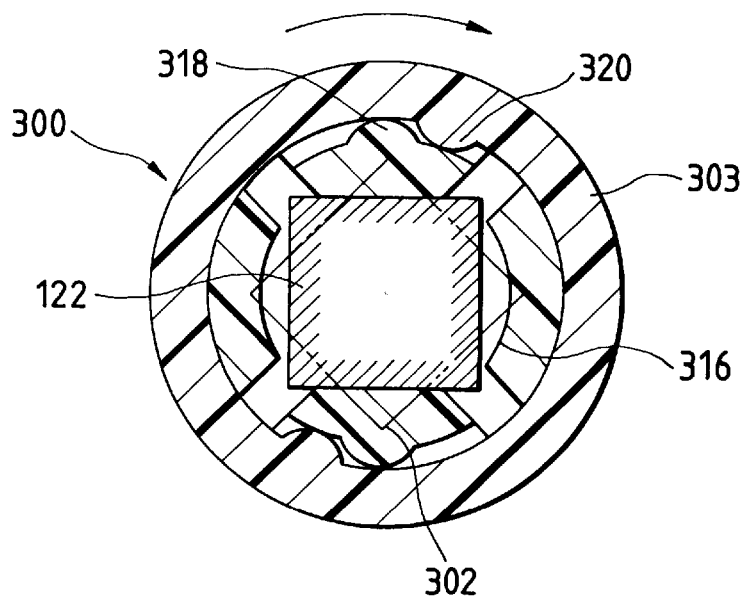
FIG. 24 is a cross-sectional view taken along a plane perpendicular to the axis of the joint, showing a state in which the non-HF sheath is connected to the non-HF manipulating section.
Figure 25:
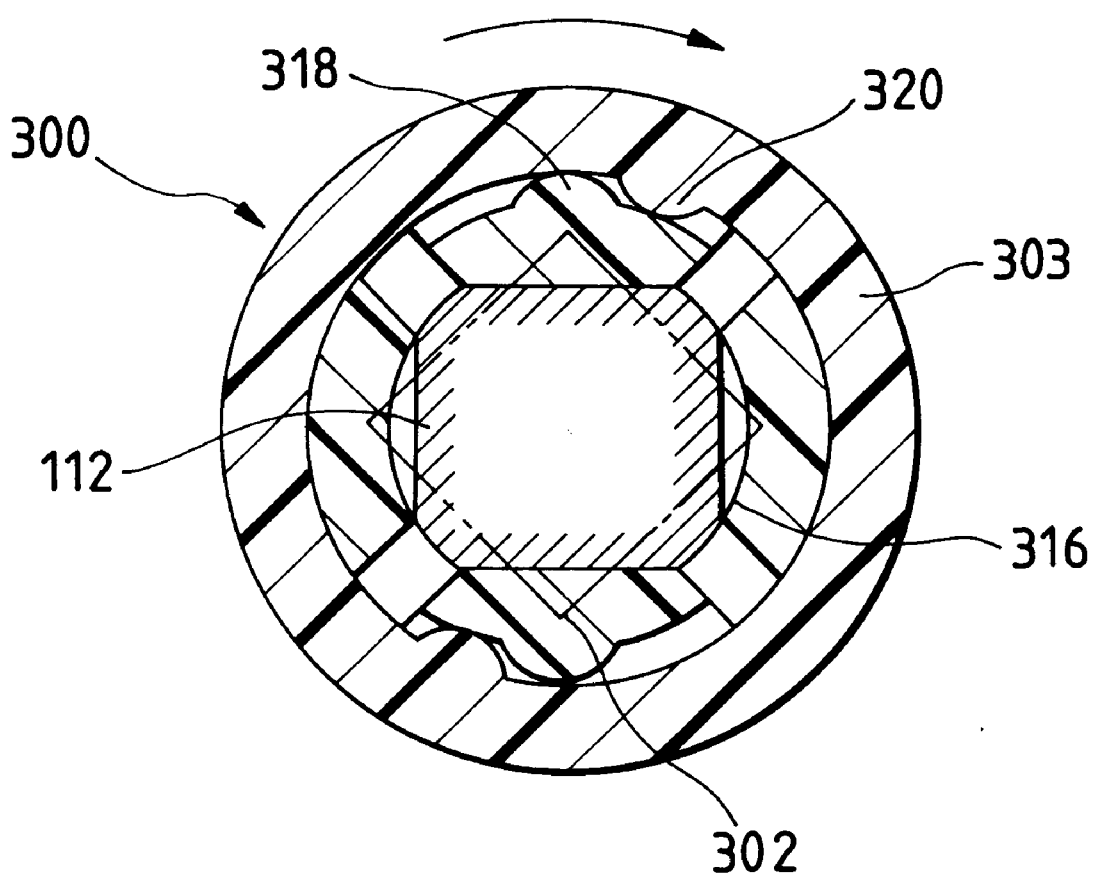
FIG. 25 is a cross-sectional view taken along a plane perpendicular to the axis of the joint, showing a state in which the compatible sheath is connected to the non-HF manipulating section.

FIG. 24 shows a state in which the non-HF joint 122 of the non-HF sheath 120 is connected to the non-HF manipulating section 300, and FIG. 25 shows a state in which the joint 112 of the compatible sheath 110 is connected to the non-HF manipulating section 300.

In each of the states, since the non-HF receptacle ring 303 has been rotated by 45° until the clicking protrusions 320 have passed across the clicking protrusions 318 to thereby rotate the non-HF insertion hole 302 as shown by two-dot chain line, neither of the joint 112 and the non-HF joint 122 can be removed from the inside of the insertion hole 316. Therefore, either of the compatible sheath 110 or the non-HF sheath 120 can be connected to the non-HF manipulating section 300.

So long as the non-HF receptacle ring 303 is reversely rotated until it returns to its original position shown in FIG. 23, the joint 112 or the non-HF joint 122 can be removed from the insertion hole 316, and therefore the compatible sheath 110 or the non-HF sheath 120 can be disconnected from the non-HF manipulating section 300.

Figure 26:
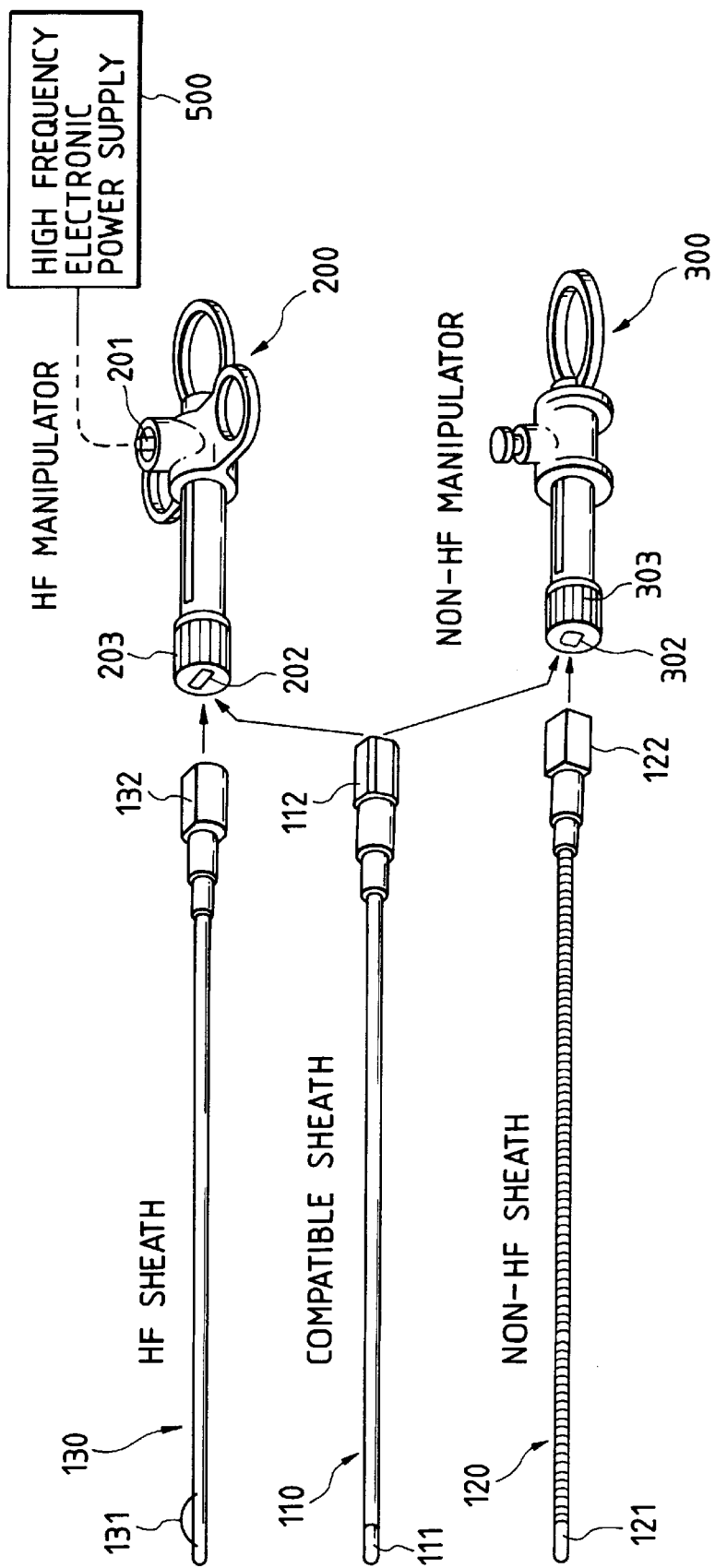
FIG. 26 is a perspective view showing an endoscopic treatment system using a joint mechanism according to further another embodiment.

FIG. 26 shows another endoscopic treatment system using a joint mechanism, which additionally includes a sheath 130 dedicated for the high frequency treatment (hereinafter referred to simply as a "HF sheath").

The HF sheath 130 is equipped with a treatment tool which is not to be used without application of a high frequency current. For example, the high frequency sheath 130 constitutes a high frequency incising tool (e.g., so-called a papyrotomy knife).

The treatment member 131 at the distal end of the HF sheath 130 is constructed, for instance, by a single conductive wire exposed and bulged from the HF sheath 131. The outer surface of the HF sheath 130 is covered with an electrically insulating member such as a tetrafluoroethylene resin tube.

Figure 27:
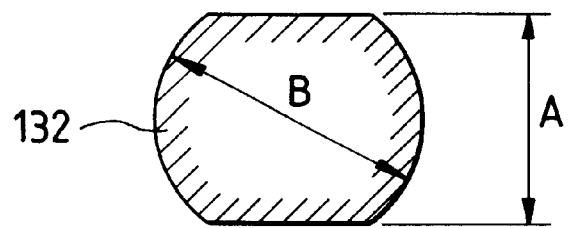
FIG. 27 is a cross sectional view taken along a plane perpendicular to the axis of an HF joint used in the system shown in FIG. 26.

As shown in FIG. 27, the HF joint 132 attached to the base end of the HF sheath 130 has an oblong cross section which is identical in shape and dimension to the cross section shape of the HF insertion hole 202.

Figure 28:
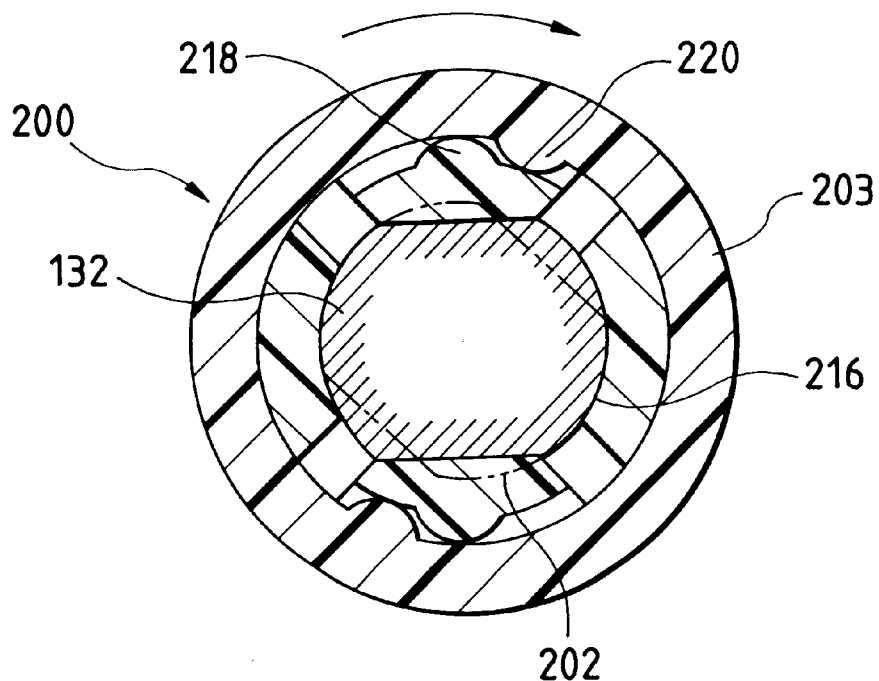
FIG. 28 is a cross-sectional view taken along a plane perpendicular to the axis of the joint, showing a state in which an HF sheath is connected to the HF manipulating section.

Accordingly, the HF sheath 130 can be connected to or removed from the HF manipulating section 200 as shown in FIG. 28, but since the HF joint 132 cannot pass through the non-HF insertion hole 302, the HF joint 132 cannot be connected to the non-HF manipulating section 300.

In addition, although not illustrated, the joint 132 is formed with an annular groove as a constricted portion adjacent the oblong cross section portion so as to receive the edges of the receptacle ring 103 around the HF insertion hole 202 when the receptacle ring 203 is rotated in a state that the oblong cross section portion is fitted into the insertion hole 206.

Each of the endoscopic treatment systems described above requires only two types of manipulating sections, i.e. an HF manipulating section provided with a high frequency power connection terminal, and a non-HF manipulating section having no high frequency power connection terminal. For these manipulating sections, at least two types of sheaths are provided, one of which is a compatible sheath which can be connected to either of the HF manipulating section and the non-HF manipulating section, and the other of which is a non-HF sheath which can be connected to the non-HF manipulating section but never be connected to the HF manipulating section. Therefore, the risk caused by erroneously connecting the non-HF sheath to the HF manipulating section can be surely is eliminated, and the endoscopic treatment can be performed with safety. Further, since the joint mechanism does not depend on the elastic deformation of the components when the sheath is connected completely to the manipulating section, even if the sheath is left for a long period of time or subjected to sterilization in an autoclave while remaining connected to the manipulating section, any components of the sheath and the manipulating section will not become deformed, thereby maintaining superior operability.

What is claimed is:

1. A joint mechanism connecting between a sheath and a manipulating section of an endoscopic treatment instrument, said joint mechanism comprising:

a first insertion hole on an end of said manipulating section to be connected to said sheath, said first insertion hole having a first cross sectional shape; and a receptacle ring provided on said end of said manipulating section and rotatable between first and second positions relative to said end of said manipulating section, said receptacle ring having a second insertion hole aligned with respect to said first insertion hole, said second insertion hole having a second cross sectional shape;

a joint on an end of said sheath to be connected to said manipulating section, said joint including an expanded portion having a third cross sectional shape, and a constricted portion having a fourth cross sectional shape and located between said expanded portion and said sheath;

wherein a first common sectional shape defined cooperatively by said first and second cross sectional shapes when said receptacle ring is in said first position is substantially equal to or larger than said fourth cross sectional shape, and at least partially smaller than said third cross sectional shape; and wherein a second common sectional shape defined cooperatively by said first and second cross sectional shapes when said receptacle ring is in said second position is substantially equal to or larger than said third cross sectional shape.

2. The joint mechanism according to claim 1, wherein said expanded portion is adapted to be non-rotatably received by said first insertion hole.

3. The joint mechanism according to claim 1, wherein each of said second and third cross sectional shape is rectangular.

4. The joint mechanism according to claim 1, wherein each of said second and third cross sectional shape is oblong.

5. The joint mechanism according to claim 1, wherein said second cross sectional shape is oblong and said third cross sectional shape is rectangular, said third cross sectional shape including rounded corner portions.

6. The joint mechanism according to claim 1, wherein said second cross sectional shape is rectangular and said third cross sectional shape is rectangular, said third cross sectional shape including rounded corner portions.

7. The joint mechanism according to claim 1, further comprising:

said end of said manipulating section is divided by a plurality of slits into a plurality of split pieces;

a first protrusion on an inner circumferential surface of said receptacle ring;

a second protrusion on an outer circumferential surface of one of said split pieces, wherein during rotation of said receptacle ring from said first position to said second position or vice versa, said first protrusion passes across said second protrusion while elastically deforming said one of said split pieces radially inwardly through said second protrusion, and then disposed adjacent to said second protrusion so that said one of said split pieces elastically returns to its original state where no elastic deformation is caused on said one of said split pieces and that said receptacle ring is retained in said position.

8. An endoscopic treatment system using a joint mechanism, said system comprising:

first and second discrete manipulating sections, each including:

a first insertion hole on an end of said manipulating section, said first insertion hole having a first cross sectional shape; and a receptacle ring provided on said end of said manipulating section and rotatable between first and second positions relative to said end of said manipulating section, said receptacle ring having a second insertion hole aligned with respect to said first insertion hole, said second insertion hole having a second cross sectional shape;

and second discrete sheaths, each including:

a joint on an end of said sheath, said joint including an expanded portion having a third cross sectional shape, and a constricted portion having a fourth cross sectional shape and located between said expanded portion and said sheath;

wherein a first common sectional shape defined cooperatively by said first and second cross sectional shapes of said first manipulating section when said receptacle ring of said first manipulating section is in said first position is substantially equal to or larger than said fourth cross sectional shape of said first sheath, and at least partially smaller than said third cross sectional shape of said first sheath;

wherein a second common sectional shape defined cooperatively by said first and second cross sectional shapes of said first manipulating section when said receptacle ring of said first manipulating section is in said second position is substantially equal to or larger than said third cross sectional shape of said first sheath;

wherein a third common sectional shape defined cooperatively by said first and second cross sectional shapes of said second manipulating section when said receptacle ring of said second manipulating section is in said first position is substantially equal to or larger than said fourth cross sectional shape of said first sheath, and at least partially smaller than said third cross sectional shape of said first sheath;

wherein a fourth common sectional shape defined cooperatively by said first and second cross sectional shapes of said second manipulating section when said receptacle ring of said second manipulating section is in said second position is substantially equal to or larger than said third cross sectional shape of said first sheath;

wherein each of said first and second common sectional shapes is at least partially smaller than said third cross sectional shape of said second sheath;

wherein said third common sectional shape is substantially equal to or larger than said fourth cross sectional shape of said second sheath, and at least partially smaller than said third cross sectional shape of said second sheath; and wherein said fourth common sectional shape is substantially equal to or larger than said third cross sectional shape of said second sheath.

9. The system according to claim 8, wherein said second cross sectional shape of said first manipulating section is oblong, said third cross sectional shape of said first sheath is rectangular, said third cross sectional shape including rounded corner portions, and each of said second cross sectional shape of said second manipulating section and said third cross sectional shape of said second sheath is rectangular.

10. The system according to claim 9, wherein said first manipulating section has an electric power connection terminal for cauterization, and said second manipulating section has no electric power connection terminal for cauterization.

11. The system according to claim 10, wherein said electric power connection terminal for cauterization is to be connected to a high-frequency electric power supply.

12. The system according to claim 8, wherein said second cross sectional shape of said first manipulating section is rectangular, said third cross sectional shape of said first sheath is rectangular, said third cross sectional shape including rounded corner portions, and each of said second cross sectional shape of said second manipulating section and said third cross sectional shape of said second sheath is oblong.

13. The system according to claim 12, wherein said first manipulating section has no electric power connection terminal for cauterization, and said second manipulating section has an electric power connection terminal for cauterization.

14. The system according to claim 13, wherein said electric power connection terminal for cauterization is to be connected to a high-frequency electric power supply.

15. The system according to claim 8, wherein an outer surface of said first sheath is covered with an elastically insulative material, and an exposed outer surface of said second sheath is electrically conductive.

16. The system according to claim 8, wherein said first manipulating section is a manipulating section for electric cauterization, said second manipulating section is a manipulating section not for electric cauterization, said first sheath is a compatible sheath, and said second sheath is a sheath not for electric cauterization.

17. The system according to claim 16, wherein said manipulating section for electric cauterization is connectable to a high-frequency electric power supply, and said manipulating section not for electric cauterization is not connectable to said high-frequency electric power supply.

18. The system according to claim 8, wherein said first manipulating section is a manipulating section not for electric cauterization, said second manipulating section is a manipulating section for electric cauterization, said first sheath is a compatible sheath, and said second sheath is a sheath for electric cauterization.

19. The system according to claim 18, wherein said manipulating section for electric cauterization is connectable to a high-frequency electric power supply, and said manipulating section not for electric cauterization is not connectable to said high-frequency electric power supply.

20. A joint mechanism for connecting between a sheath and a manipulating section of an endoscopic treatment instrument, said mechanism comprising:

a joint including a leading end portion connected to said sheath, and an expanded base end portion having a first cross sectional shape;

a receptacle ring mounted on an leading end portion of said manipulating section and rotatable within a predetermined angular range relative to said leading end portion of said manipulating section, said receptacle ring being formed with an insertion hole having such a second cross section as to permit said expanded base end portion to be passed therethrough; and a fitting hole, formed in said leading end portion of said manipulating section, for non-rotatably receiving said expanded base end portion that has been passed through the insertion hole;

wherein by rotating said receptacle ring in a state that said expanded base end portion has been passed through said insertion hole and fitted in said fitting hole, said insertion hole is oriented to inhibit passage of said expanded base end portion therethrough, thereby non-removably connect said joint to said leading end portion of said manipulating section.

21. An endoscopic treatment system using a joint mechanism, said system comprising:

a manipulating section for electric cauterization, provided with an electric power connection terminal;

a manipulating section not for electric cauterization, which is not provided with an electric power connection terminal;

a compatible sheath which can be connected to either of said manipulating sections; and a sheath not for electric cauterization, which can be connected to said manipulating section not for electric cauterization, but cannot be connected to said manipulating section for electric cauterization.

22. The system according to claim 21, wherein said manipulating section for electric cauterization is connectable to a high-frequency electric power supply, and said manipulating section not for electric cauterization is not connectable to said high-frequency electric power supply.

* * * * *

UNITED STATES PATENT AND TRADEMARK OFFICE
CERTIFICATE OF CORRECTION

PATENT NO. : 6,113,586
DATED : September 5, 2000
INVENTOR(S) : T. OUCHI

It is certified that error appears in the above-identified patent and that said Letters Patent is hereby corrected as shown below:

On the cover of the printed patent, at Item [73], Assignee, after "Kogaku" insert ---Kogyo---.

Signed and Sealed this

Eighth Day of May, 2001

Attest:

NICHOLAS P. GODICI

Attesting Officer   Acting Director of the United States Patent and Trademark Office